(12) United States Patent
Vidal

(10) Patent No.: US 6,881,230 B2
(45) Date of Patent: Apr. 19, 2005

(54) DYEING COMPOSITION FOR DYEING KERATINOUS FIBERS COMPRISING A CATIONIC AZO-DYE

(75) Inventor: Laurent Vidal, Paris (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 10/473,611

(22) PCT Filed: Apr. 2, 2002

(86) PCT No.: PCT/FR02/01136

§ 371 (c)(1),
(2), (4) Date: Jan. 22, 2004

(87) PCT Pub. No.: WO02/078658

PCT Pub. Date: Oct. 10, 2002

(65) Prior Publication Data

US 2004/0168263 A1 Sep. 2, 2004

(30) Foreign Application Priority Data

Apr. 2, 2001 (FR) .............................. 01 04467

(51) Int. Cl.$^7$ ................................................ A61K 7/13
(52) U.S. Cl. ...................... 8/405; 8/407; 8/437; 8/451; 8/463; 8/466; 8/570; 8/573; 8/574; 548/318.1; 548/321.1; 540/450

(58) Field of Search ............................ 8/405, 407, 437, 8/451, 463, 466, 570, 572, 573, 574; 548/318.1, 321.1; 540/450

(56) References Cited

U.S. PATENT DOCUMENTS

| 5,879,412 A | * 3/1999 | Rondeau et al. ................ 8/411 |
| 5,919,273 A | 7/1999 | Rondeau et al. ................ 8/412 |

FOREIGN PATENT DOCUMENTS

| BE | 580 029 | 10/1959 |
| EP | 0 850 636 | 7/1998 |
| EP | 0 852 135 | 7/1998 |

* cited by examiner

Primary Examiner—Margaret Einsmann
Assistant Examiner—Eisa Elhilo
(74) Attorney, Agent, or Firm—Finnegan, Henderson, Farabow, Garrett & Dunner, L.L.P.

(57) ABSTRACT

The invention concerns a novel dyeing composition for dyeing keratinous fibers, in particular human hair, comprising a cationic azo-dye of formula (I): W1-N=N-W2-W3, as well as the dyeing method using said composition and the novel compounds of formula (I).

37 Claims, No Drawings

DYEING COMPOSITION FOR DYEING KERATINOUS FIBERS COMPRISING A CATIONIC AZO-DYE

A subject matter of the invention is a novel dyeing composition for the dyeing of keratinous fibers, in particular of human hair, comprising a specific cationic azo dye and the process for dyeing keratinous fibers employing such a composition. Another subject matter of the invention is novel cationic azo dyes.

It is known to dye keratinous fibers and in particular human hair with dyeing compositions comprising oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing substances, give rise to colored compounds by an oxidative coupling process.

It is also known that the hues obtained with these oxidation bases can be varied by combining them with couplers or coloring modifiers, the latter being chosen in particular from aromatic meta-diamines, meta-aminophenols meta-diphenols and certain heterocyclic compounds, such as indole compounds.

The variety of the molecules employed as oxidation bases and couplers makes it possible to obtain a rich palette of colors.

This oxidation dyeing process consists in applying, to the keratinous fibers, oxidation bases or a mixture of oxidation bases and of couplers with an oxidizing agent, for example aqueous hydrogen peroxide solution, in leaving to stand and in then rinsing the fibers. The colorations which result therefrom are permanent and powerful, and withstand external agents, in particular light, bad weather, washing, perspiration and rubbing. Generally applied at basic pH, they make it possible to obtain dyeing and simultaneously lightening of the fiber, which is reflected in practice by the possibility of obtaining a final coloration which is lighter than the original color. In addition, lightening the fiber has the advantageous effect of producing a unified color in the case of gray hair and, in the case of naturally pigmented hair, of making the color emerge, that is to say of rendering it more visible.

It is also known to dye human keratinous fibers by direct dyeing. The process conventionally used in direct dyeing consists in applying, to the keratinous fibers, direct dyes, which are colored and coloring molecules having an affinity for the fibers, in leaving to stand and in then rinsing the fibers.

It is known, for example, to use nitrobenzene, anthraquinone or nitropyridine direct dyes, azo, xanthene, acridine or azine dyes or triarylmethane dyes.

The colorations which result therefrom are particularly chromatic colorations which, however, are temporary or semipermanent because the nature of the interactions which bind the direct dyes to the keratinous fiber and their desorption from the surface and/or from the core of the fiber are responsible for their low dyeing power and for their poor resistance to washing or to perspiration. In addition, these direct dyes are generally sensitive to light, because of the low resistance of the chromophore with regard to photochemical attacks, and result over time in fading of the coloring of the hair. In addition, their sensitivity to light is dependent on their distribution, uniform or nonuniform, in the keratinous fiber.

It is known to use direct dyes in combination with oxidizing agents. However, direct dyes are generally sensitive to the action of oxidizing agents, such as aqueous hydrogen peroxide solution, and reducing agents, such as sodium bisulfite, which generally renders them difficult to use in compositions for lightening direct dyeing based on aqueous hydrogen peroxide solution and based on a basifying agent or in oxidation dyeing compositions in combination with oxidation dye precursors or couplers.

For example, provision has been made, in Patent Applications FR-1 584 965 and JP-062 711 435, to dye the hair with dyeing compositions based on direct nitro dyes and/or on disperse azo dyes and on aqueous ammoniacal hydrogen peroxide solution by applying, to the hair, a mixture of said dyes and of said oxidizing agent prepared immediately before use. However, the colorations obtained prove to be insufficiently persistent and disappear on shampooing, allowing the lightening of the hair fiber to become apparent. Such a coloration becomes unattractive on changing over time.

Provision has also been made, in Patent Applications JP-53 95693 and JP 55 022638, to dye the hair with compositions based on cationic direct dyes of oxazine type and on aqueous ammoniacal hydrogen peroxide solution by applying, to the hair, in a first stage, aqueous ammoniacal hydrogen peroxide solution and then, in a second stage, a composition based on the direct oxazine dye. This coloration is not satisfactory because of the fact that it requires a process rendered excessively slow by the leave-in times of the two successive stages. Furthermore, if a mixture prepared at the time of use of the direct oxazine dye with aqueous ammoniacal hydrogen peroxide solution is applied to the hair, no coloration is produced or, at least, a coloration of the hair fiber is obtained which is virtually nonexistent.

More recently, Patent Application FR 2 741 798 has disclosed dyeing compositions comprising direct azo or azomethine dyes comprising at least one quaternized nitrogen atom, said compositions having to be mixed at the time of use at basic pH with an oxidizing composition. These compositions make it possible to obtain colorations with homogeneous, persistent and bright highlights. However, they do not make it possible to dye keratinous fibers with as much power as with oxidation dyeing compositions.

There thus exists a real need to try to find chromatic direct dyes which make it possible to dye keratinous fibers as powerfully as oxidation dyes, which are as stable as them toward light and are also resistant to bad weather, washing and perspiration, and which, in addition, are sufficiently stable in the presence of oxidizing and reducing agents to be able to simultaneously obtain lightening of the fiber, either by use of lightening direct compositions comprising them or by the use of oxidation dyeing compositions comprising them. There also exists a real need to try to find direct dyes which make it possible to dye keratinous fibers in order to obtain a very broad range of colors, in particular highly chromatic colors, without forgetting the "basic" shades, such as the blacks and the browns.

These aims are achieved with the present invention, a subject matter of which is a composition for dyeing keratinous fibers, and in particular human keratinous fibers such as the hair, comprising at least one cationic azo dye of the following formula (I):

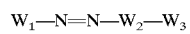

in which $W_1$ represents a 5-membered cationic aromatic heterocycle of the following formula (II)

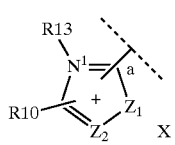

formula (II)

$W_2$ represents a divalent carbonaceous aromatic or pyridine group of the following formulae (III) or (IV)

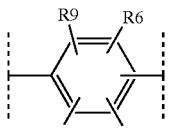

formula (III)

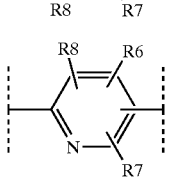

formula (IV)

$W_3$ represents a 7- or 8-membered heterocycle of the following formula (V)

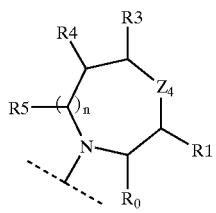

formula (V)

in which formulae $Z_1$ represents an oxygen or sulfur atom or a radical $NR_{12}$, $Z_2$ represents a nitrogen atom or a radical $CR_{11}$, $R_{12}$ and $R_{13}$ represent, independently of one another, a $C_1$–$C_8$ alkyl radical optionally substituted by one or more radicals chosen from a hydroxyl, a $C_1$–$C_2$ alkoxy, a $C_2$–$C_4$ (poly)hydroxyalkoxy radical, an amino, a $C_1$–$C_2$ (di)alkylamino, a carboxyl or a sulfonic; an optionally substituted phenyl radical, $R_{10}$ and $R_{11}$ represent, independently of one another, a hydrogen atom; a $C_1$–$C_4$ alkyl radical, optionally substituted by one or more radicals chosen from a hydroxyl, a $C_1$–$C_2$ alkoxy, a $C_2$–$C_4$ (poly)hydroxyalkoxy radical, an amino, a $C_1$–$C_2$ (di)alkylamino, a carboxyl or a sulfonic; an optionally substituted phenyl radical; a carboxyl radical; a sulfonylamino radical;

$R_6$, $R_7$, $R_8$ and $R_9$ represent, independently of one another, a hydrogen atom; a chlorine atom; a bromine atom; a linear or branched $C_1$–$C_6$ hydrocarbonaceous chain which can form one or more 3- to 6-membered carbonaceous rings and which can be saturated or unsaturated, of which one or more carbon atoms of the carbonaceous chain can be replaced by an oxygen, nitrogen or sulfur atom or by an $SO_2$ group, and the carbon atoms of which can be, independently of one another, substituted by one or more halogen atoms; $R_6$, $R_7$, $R_8$ and $R_9$ not comprising a peroxide bond or diazo or nitroso radicals, n is an integer equal to 1 or 2, $Z_4$ represents an oxygen or sulfur atom, a radical $NR_2$ or a radical $CR_2R_2'$, $R_0$, $R_1$, $R_2$, $R_2'$, $R_3$, $R_4$ and $R_5$ represent, independently of one another, a hydrogen atom; an alkyl radical; an alkoxy radical; a hydroxyl radical; amino; acetoxy; a group —$NR_{14}R_{15}$, $R_{14}$ and $R_{15}$ representing, independently of one another, a hydrogen atom, a $C_1$–$C_4$ alkyl radical substituted by one or more radicals chosen from a halogen atom, a hydroxyl, $C_1$–$C_2$ alkoxy, amino or $C_1$–$C_2$ amino(di)alkyl radical; a sulfonylamino radical; a carboxyl radical; a carboxamido radical; an amido radical; a mono- or dialkylamido radical; a halogen; a $C_1$–$C_6$ alkyl radical substituted by one or more radicals chosen from a hydroxyl, $C_1$–$C_2$ alkoxy, $C_2$–$C_4$ (poly) hydroxyalkoxy, amino and $C_1$–$C_2$ (di)alkylamino radical, X is an organic or inorganic anion.

In the context of the present invention, the term "alkyl", unless otherwise stated, is understood to mean an alkyl radical comprising from 1 to 10 carbon atoms, preferably from 1 to 6 carbon atoms, which may be linear or branched. The term alkoxy means alkyl-O—, the term alkyl having the above meaning.

According to the invention, when it is indicated that one or more of the carbon atoms of the hydrocarbonaceous chain defined for the radicals $R_6$ to $R_9$ can be replaced by an oxygen, nitrogen or sulfur atom or by an $SO_2$ group, and/or that these hydrocarbonaceous chains are unsaturated, this means that it is possible, by way of example, to carry out the following conversions:

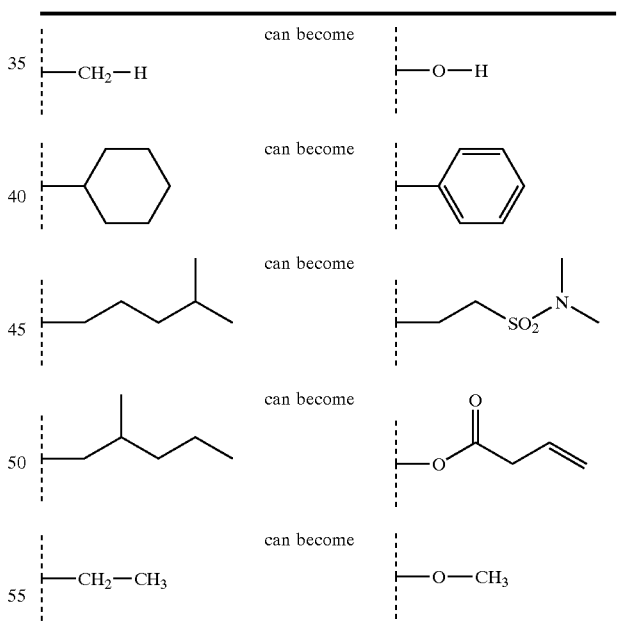

In particular, the expression "branched hydrocarbonaceous chain" is understood to mean a chain which can form one or more 3- to 6-membered carbonaceous rings. The expression unsaturated hydrocarbonaceous chain is understood to mean a chain which can comprise one or more double bonds and/or one or more triple bonds, it being possible for this hydrocarbonaceous chain to lead to aromatic groups.

The asymmetric carbons substituted by the $R_0$, $R_1$, $R_2$, $R_3$, $R_4$ and $R_5$ radicals can be of the (R) and/or (S) configuration.

According to the invention, $R_0$, $R_1$, $R_2$, $R_3$, $R_4$ and $R_5$ preferably represent a hydrogen, a $C_1$–$C_4$ alkyl radical, a $C_1$–$C_4$ alkoxy radical, a hydroxyl, acetoxy, amino, methylamino, dimethylamino, 2-hydroxyethylamino, carboxyl, carboxamido or amido radical.

According to a particular embodiment, $R_0$, $R_1$, $Z_4$, $R_3$, $R_4$, $R_5$ and n are chosen from the following combinations:

| $R_0$ | $R_1$ | $Z_4$ | $R_3$ | $R_4$ | $R_5$ | n |
|---|---|---|---|---|---|---|
| COOH | H | CH$_2$ | H | H | H | 1 or 2 |
| COOH | OH | CH$_2$ | H | H | H | 1 or 2 |
| H | H | CH$_2$ | H | H | H | 1 or 2 |
| CONH2 | H | CH$_2$ | H | H | H | 1 or 2 |
| CONH2 | OH | CH$_2$ | H | H | H | 1 or 2 |
| CONMe2 | H | CH$_2$ | H | H | H | 1 or 2 |
| CONMe2 | OH | CH$_2$ | H | H | H | 1 or 2 |
| CH2OH | H | CH$_2$ | H | H | H | 1 or 2 |
| CH2OH | OH | CH$_2$ | H | H | H | 1 or 2 |
| CH2OH | H | CH$_2$ | CH2OH | H | H | 1 |
| H | OH | CH$_2$ | H | H | H | 1 or 2 |
| H | OH | CH—OH | H | H | H | 1 or 2 |
| H | NH2 | CH$_2$ | H | H | H | 1 or 2 |
| H | NHMe | CH$_2$ | H | H | H | 1 or 2 |
| H | NMe2 | CH$_2$ | H | H | H | 1 or 2 |
| H | OH | CH—NH$_2$ | H | H | H | 1 or 2 |
| H | OH | CH—NHMe | H | H | H | 1 or 2 |
| H | OH | CH—NH—CH$_2$—CH—OH | H | H | H | 1 or 2 |
| H | H | NH | H | H | H | 1 or 2 |
| H | H | NMe | H | H | H | 1 or 2 |
| H | H | N—CH$_2$—CH$_2$—OH | H | H | H | 1 or 2 |

Preferably, $R_0$, $R_1$, $Z_4$, $R_3$, $R_4$ and $R_5$ are chosen from the following combinations:

| $R_0$ | $R_1$ | $Z_4$ | $R_3$ | $R_4$ | $R_5$ |
|---|---|---|---|---|---|
| H | H | CH$_2$ | H | H | H |
| COOH | H | CH$_2$ | H | H | H |
| COOH | OH | CH$_2$ | H | H | H |
| CONMe2 | H | CH$_2$ | H | H | H |
| CH2OH | H | CH$_2$ | H | H | H |
| CH2OH | OH | CH$_2$ | H | H | H |
| H | OH | CH$_2$ | H | H | H |
| H | NH2 | CH$_2$ | H | H | H |
| H | H | NH | H | H | H |
| H | H | NMe | H | H | H |

The radicals $R_6$, $R_7$, $R_8$ and $R_9$ are preferably chosen from a hydrogen atom, a methyl, ethyl, isopropyl, methoxymethyl, hydroxymethyl, 1-carboxymethyl, 1-aminomethyl, 1-aminoethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 3-hydroxyethyloxy, 3-aminoethyloxy, amino, methylamino, dimethylamino and 2-hydroxyethylamino radical. According to a preferred embodiment, $R_6$, $R_7$, $R_8$ and $R_9$ are chosen from a hydrogen atom, a methyl, hydroxymethyl, 2-hydroxyethyl, 1,2-dihydroxyethyl, methoxy, 2-hydroxyethoxy, amino and 2-hydroxyethylamino radical, more preferably a hydrogen atom, a methyl radical, a methoxy radical and an amino radical.

According to the invention, $R_{12}$ and $R_{13}$ preferably represent a $C_1$–$C_4$ alkyl radical, optionally substituted by one or more radicals chosen from a hydroxyl, a $C_1$–$C_2$ alkoxy, an amino, a $C_1$–$C_2$ (di)alkylamino, a carboxyl, a phenyl radical, a sulfonic, more preferably a methyl, ethyl, 2-hydroxyethyl, 1-carboxymethyl, 2-carboxyethyl and 2-sulfonylethyl radical.

According to the invention, $R_{10}$ and $R_{11}$ preferably represent a hydrogen atom, a $C_1$–$C_4$ alkyl radical optionally substituted by one or more radicals chosen from a hydroxyl, an amino, a $C_1$–$C_2$ (di)alkylamino, a carboxyl and a phenyl, preferably $R_{10}$ and $R_{11}$ represent a hydrogen atom, a methyl, ethyl, 2-hydroxyethyl, carboxyl, 1-carboxymethyl, 2-carboxyethyl or 2-sulfonylethyl radical.

In formula (II), $Z_1$ is preferably —$NR_{12}$ and $Z_2$ is preferably $CR_{11}$.

According to a particular embodiment of the formula (V), $Z_4$ is $NR_2$ or $CR_2$.

The organic or inorganic anion X may be chosen from a halide such as chloride, bromide, fluoride, iodide; a hydroxide; a sulfate; a hydrogen sulfate; a ($C_1$–$C_6$)alkyl sulfate such as for example a methyl sulfate or an ethyl sulfate; an acetate; a tartrate; an oxalate; a ($C_1$–$C_6$)alkyl sulfonate such as methyl sulfonate; an aryl sulfonate which is unsubstituted or substituted by a $C_1$–$C_4$ alkyl radical such as for example a 4-toluoyl sulfonate.

The concentration of cationic azo dye of formula (I) can vary between 0.001 and 5% by weight approximately relative to the total weight of the dyeing composition, and preferably between approximately 0.05 and 2%.

The composition of the invention can furthermore comprise an oxidizing agent. This oxidizing agent can be any oxidizing agent conventionally used for bleaching keratinous fibers. The oxidizing agent is preferably chosen from hydrogen peroxide, urea peroxide, alkali metal bromates, persalts such as perborates and persulfates. The use of hydrogen peroxide is particularly preferred.

The composition according to the invention can furthermore comprise an oxidation base. This oxidation base can be chosen from the oxidation bases conventionally used in oxidation dyeing, for example para-phenylenediamines, bisphenylalkylenediamines, para-aminophenols, ortho-aminophenols and heterocyclic bases.

Mention may more particularly be made, among para-phenylenediamines, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-(aminophenyl) pyrrolidine, 2-thienyl-para-phenylenediamine, 2-(β-hydroxyethylamino)-5-aminotoluene, and their addition salts with an acid.

Among the para-phenylenediamines mentioned above, para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and their addition salts with an acid, are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts with an acid.

Mention may be made, among para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-(2-aminomethyl)phenol, 4-amino-2-[(β-hydroxy-ethyl)aminomethyl]phenol, 4-amino-2-fluorophenol, and their addition salts with an acid.

Mention may be made, among ortho-aminophenols, by way of example, of 2-aminophenol, 2-amino-5-methylphenol, 2-amino-6-methylphenol, 5-acetamido-2-aminophenol, and their addition salts with an acid.

Mention may be made, among heterocyclic bases, by way of example, of pyridine derivatives, pyrimidine derivatives and pyrazole derivatives.

Mention may be made, among pyridine derivatives, of the compounds disclosed, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Mention may be made, among pyrimidine derivatives, of the compounds disclosed, for example, in Patents DE 2 359 399, JP 88-169 571, JP 05 163 124 or EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in Patent Application FR-A-2 750 048, among which may be mentioned pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine, and their addition salts with an acid and their tautomeric forms, when a tautomeric equilibrium exists.

Mention may be made, among pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and their addition salts with an acid.

The composition according to the invention can additionally comprise one or more couplers conventionally used for the conventional oxidation dyeing of keratinous fibers. Mention may in particular be made, among these couplers, of meta-phenylenediamines, meta-aminophenols, meta-diphenols, naphthalene couplers and heterocyclic couplers.

Mention may be made, by way of example, of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts with an acid.

In the composition of the present invention, the coupler or couplers are generally present in an amount of between 0.001 and 10% by weight approximately of the total weight of the dyeing composition and more preferably from 0.005 to 6%. The oxidation base or bases are present in an amount preferably of between 0.001 and 10% by weight approximately of the total weight of the dyeing composition and more preferably from 0.005 to 6%.

Generally, the addition salts with an acid which can be used in the context of the dyeing compositions of the invention for the oxidation bases and the couplers are chosen in particular from hydrochlorides, hydrobromides, sulfates, citrates, succinates, tartrates, lactates, tosylates, benzenesulfonates, phosphates and acetates.

The dyeing composition in accordance with the invention can additionally contain direct dyes different from those of formula (I), it being possible for these dyes in particular to be chosen from nitro dyes of the benzene series, cationic direct dyes, direct azo dyes and direct methine dyes.

The medium acceptable for dyeing, also referred to as dyeing support, is generally composed of water or of a mixture of water and of at least one organic solvent, in order to dissolve the compounds which would not be sufficiently soluble in water. Mention may be made, as organic solvent, for example, of lower $C_1$–$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol; and their mixtures.

The solvents can be present in proportions preferably of between 1 and 40% by weight approximately with respect to the total weight of the dyeing composition and more preferably still between 5 and 30% by weight approximately.

The dyeing composition in accordance with the invention can also include various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents and in particular anionic, cationic, nonionic and amphoteric associative polymer thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives or opacifying agents.

These above adjuvants are generally present in an amount of, for each of them, between 0.01 and 20% by weight with respect to the weight of the composition.

Of course, a person skilled in the art will take care to choose this or these optional additional compounds so that the advantageous properties intrinsically attached to the dyeing composition in accordance with the invention are not, or not substantially, detrimentally affected by the envisaged addition or additions.

The pH of the dyeing composition in accordance with the invention is generally between 3 and 12 approximately and preferably between 5 and 11 approximately. It can be adjusted to the desired value by means of acidifying or basifying agents commonly used in dyeing keratinous fibers or alternatively using conventional buffer systems.

Mention may be made, among acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Mention may be made, among basifying agents, by way of example, of ammonia, alkaline carbonates, alkanolamines, such as mono-, di- and triethanolamines, and their derivatives, sodium hydroxide, potassium hydroxide and the compounds of following formula (III):

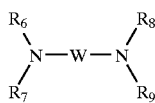

(III)

in which W is a propylene residue optionally substituted by a hydroxyl group or a $C_1$–$C_4$ alkyl radical and $R_6$, $R_7$, $R_8$ and $R_9$, which are identical or different, represent a hydrogen atom or a $C_1$–$C_4$ alkyl or $C_1$–$C_4$ hydroxyalkyl radical.

The dyeing composition according to the invention can be provided in various forms, such as in the form of liquids, creams or gels or in any other form appropriate for carrying out dyeing of keratinous fibers and in particular of human hair.

Another subject matter of the invention is a direct dyeing process which comprises the application of a dyeing composition comprising a dye of formula (I) as defined above to keratinous fibers. After a leave-in time, the keratinous fibers are rinsed, allowing colored fibers to appear.

The application to the fibers of the dyeing composition comprising the cationic azo dye of formula (I) can be carried out in the presence of an oxidizing agent which brings about the bleaching of the fiber. This oxidizing agent can be added to the composition comprising the cationic azo dye at the time of use or directly to the keratinous fiber. According to a specific embodiment, the composition comprising the cationic azo dye of formula (I) is free of oxidation base and of coupler.

Another subject matter of the invention is an oxidation dyeing process which comprises the application to fibers of a dyeing composition which comprises a dye of formula (I), at least one oxidation base and optionally at least one coupler, in the presence of an oxidizing agent.

The oxidation base, the coupler and the oxidizing agent are as defined above.

In the context of permanent oxidation dyeing, it is also possible to use, as oxidizing agent, enzymes among which may be mentioned peroxidases, 2-electron oxidoreductases, such as uricases, and 4-electron oxygenases, such as laccases.

The color can be developed at acidic, neutral or alkaline pH and the oxidizing agent can be added to the composition of the invention either at the time of use or it can be employed from an oxidizing composition comprising it, applied to the fibers simultaneously with or sequentially to the dyeing composition.

In the case of permanent oxidation dyeing or of direct dyeing, the dyeing composition is mixed, preferably at the time of use, with a composition comprising, in a medium acceptable for dyeing, at least one oxidizing agent, this oxidizing agent being present in an amount sufficient to develop a coloring. The mixture obtained is subsequently applied to the keratinous fibers. After a leave-in time of 3 to 50 minutes approximately, preferably 5 to 30 minutes approximately, the keratinous fibers are rinsed, washed with a shampoo, rinsed again and then dried.

The oxidizing composition can also include various adjuvants conventionally used in hair dyeing compositions and as defined above.

The pH of the oxidizing composition including the oxidizing agent is such that, after mixing with the dyeing composition, the pH of the resulting composition applied to keratinous fibers preferably varies between 3 and 12 approximately, and more preferably still between 5 and 11. It can be adjusted to the desired value by means of acidifying or basifying agents commonly used in dyeing keratinous fibers and as defined above.

The composition which is finally applied to the keratinous fibers can be provided in various forms, such as in the form of liquids, creams or gels or in any other form appropriate for carrying out dyeing of keratinous fibers and in particular of human hair.

Another subject matter of the invention is a multi-compartment device or dyeing 'kit' in which a first compartment includes the dyeing composition of the invention and a second compartment includes the oxidizing composition. This device can be equipped with a means allowing the desired mixture to be delivered to the hair, such as the devices disclosed in Patent FR 2 586 913 on behalf of the Applicant Company.

Finally, another subject matter of the invention is the cationic azo dyes of formula (I) as defined above. These compounds can be obtained from the preparation processes described for example in the documents EP 810824, GB 9619573, RO 106572, J. Chem. Res., Synop. (1998), (10), 648–649, DE 19721619, U.S. Pat. No. 5,852,179, Synth. Commun 1999, 29(13), 2271–2276.

The following examples serve to illustrate the invention without, however, exhibiting a limiting nature.

EXAMPLES

Examples of Synthesis

Preparation of a compound of formula:

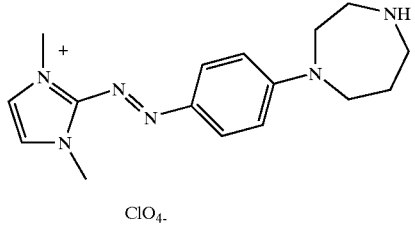

ClO$_4^-$ 2-(4-([1,4]Diazepan-1-yl)phenylazo)-1,3-dimethyl-3H-imidazol-1-ium perchlorate 5 g of homopiperazine (0.05 mol) and 6 ml of dry DMF are charged to a fully equipped round-bottomed flask. The mixture is brought to 100° C. 1.65 g of 2-(4-methoxyphenylazo)-1,3-dimethyl-3H-imidazol-1-ium perchlorate are added over 20 min. The reaction mixture is maintained for 1 hour at 100° C. with stirring and then it is allowed to cool. The reaction mixture is then poured, with stirring, into 150 ml of ethyl acetate. A precipitate forms and it is separated from a gum. This precipitate is recovered by filtration and it is washed 3 times with ethyl acetate.

A Bordeaux red powder is thus obtained.

The UV absorption characteristics of this product are the following:

UV (CH$_3$CN/H$_2$O) $\lambda_{max}$=520 nm $\epsilon_{max}$=44 000

Analyses:

Mass ESI+: m/z=299[M$^+$]

$^1$H NMR: (400 MHz-DMSO) ppm: 1.79 (m-2H); 2.66 (m-2H); 2.90 (m-2H); 3.72 (m$^{-2}$H); 3.79 (m-2H) diazepane; 3.96 (s-16H)—NCH$_3$; 7.04 (d-2H); 7.90 (d-2H) phenyl; 7.71 (s-2H); imidazole.

A dye giving a red, slightly fuchsia color is thus obtained.

What is claimed is:

1. A composition for dyeing keratinous fibers comprising at least one cationic azo dye of formula (I):

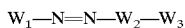    (I)

wherein:

W$_1$ is chosen from 5-membered cationic aromatic heterocycles of formula (II):

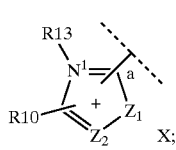    (II)

W$_2$ is chosen from divalent carbonaceous aromatic groups and pyridine groups chosen from groups of formulae (III) and (IV):

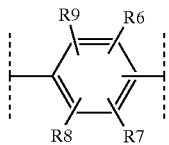    (III)

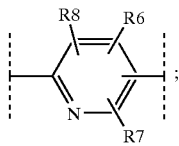    (IV)

W$_3$ is chosen from 7-membered or 8-membered heterocycles of formula (V):

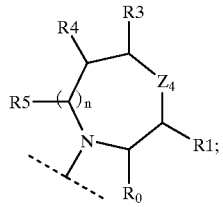    (V)

wherein:

Z$_1$ is chosen from oxygen and sulfur atoms, and NR12 radicals;

Z$_2$ is chosen from a nitrogen atom and CR11 radicals;

R12 and R13, which may be identical or different, are chosen from C$_1$–C$_8$ alkyl radicals optionally substituted with at least one radical chosen from hydroxyl radicals, C$_1$–C$_2$ alkoxy radicals, C$_2$–C$_4$ (poly) hydroxyalkoxy radicals, amino radicals, C$_1$–C$_2$ (di) alkylamino radicals, carboxyl radicals, and sulfonic radicals; and optionally substituted phenyl radicals;

R10 and R11, which may be identical or different, are chosen from hydrogen atoms, optionally substituted phenyl radicals, carboxyl radicals, sulfonylamino radicals, and C$_1$–C$_4$ alkyl radicals optionally substituted with at least one radical chosen from hydroxyl radicals, C$_1$–C$_2$ alkoxy radicals, C$_2$–C$_4$ (poly) hydroxyalkoxy radicals, amino radicals, C$_1$–C$_2$ (di) alkylamino radicals, carboxyl radicals, and sulfonic radicals;

R6, R7, R8 and R9, which may be identical or different, are chosen from hydrogen atoms; chlorine atoms; bromine atoms; linear and branched C$_1$–C$_6$ hydrocarbonaceous chains, wherein said C$_1$–C$_6$ hydrocarbonaceous chains can each form at least one saturated or unsaturated, 3- to 6-membered carbonaceous ring, wherein at least one carbon atom of each of said C$_1$–C$_6$ hydrocarbonaceous chains is optionally replaced by an entity chosen from an oxygen atom, a nitrogen atom, a sulfur atom, and an SO$_2$ radical and further wherein at least one carbon atom of each of said C$_1$–C$_6$ hydrocarbonaceous chains can be optionally substituted by at least one halogen atom, provided that R6, R7, R8, and R9, which may be identical or different, are not chosen from peroxide bonds, diazo radicals, and nitroso radicals;

n is an integer chosen from 1 and 2;

Z$_4$ is chosen from an oxygen atom, a sulfur atom, NR$_2$ radicals, and CR$_2$R$_2$' radicals;

$R_0$, $R_1$, $R_2$, $R_2'$, $R_3$, $R_4$ and $R_5$, which may be identical or different, are chosen from hydrogen atoms; alkyl radicals; alkoxy radicals; hydroxyl radicals; amino radicals; acetoxy radicals; $NR_{14}R_{15}$ groups wherein $R_{14}$ and $R_{15}$, which may be identical or different, are chosen from hydrogen atoms and $C_1$–$C_4$ alkyl radicals substituted with at least one radical chosen from halogen atoms, hydroxyl radicals, $C_1$–$C_2$ alkoxy radicals, amino radicals, and $C_1$–$C_2$ amino(di)alkyl radicals; sulfonylamino radicals; carboxyl radicals; carboxamido radicals; amido radicals; monoalkylamido radicals; dialkylamido radicals; halogen radicals; and $C_1$–$C_6$ alkyl radicals substituted with at least one radical chosen from hydroxyl radicals, $C_1$–$C_2$ alkoxy radicals, $C_2$–$C_4$ (poly)hydroxyalkoxy radicals, amino radicals and $C_1$–$C_2$ (di)alkylamino radicals; and X is chosen from organic anions and inorganic anions.

2. The composition according to claim 1, wherein said keratinous fibers are human keratinous fibers.

3. The composition according to claim 2, wherein said human keratinous fibers are hair.

4. The composition according to claim 1, wherein $R_0$, R1, $R_2$, R3, R4, and R5, which may be identical or different, are chosen from hydroxyl radicals, acetoxy radicals, amino radicals, methylamino radicals, dimethylamino radicals, 2-hydroxyethylamino radicals, carboxyl radicals, carboxamido radicals, and amido radicals.

5. The composition according to claim 1, wherein $R_0$, R1, $Z_4$, R3, R4, R5, and n, are chosen from the following combinations:

| $R_0$ | $R_1$ | $Z_4$ | $R_3$ | $R_4$ | $R_5$ | n |
|---|---|---|---|---|---|---|
| COOH | H | $CH_2$ | H | H | H | 1 or 2 |
| COOH | OH | $CH_2$ | H | H | H | 1 or 2 |
| H | H | $CH_2$ | H | H | H | 1 or 2 |
| CONH2 | H | $CH_2$ | H | H | H | 1 or 2 |
| CONH2 | OH | $CH_2$ | H | H | H | 1 or 2 |
| CONMe2 | H | $CH_2$ | H | H | H | 1 or 2 |
| CONMe2 | OH | $CH_2$ | H | H | H | 1 or 2 |
| CH2OH | H | $CH_2$ | H | H | H | 1 or 2 |
| CH2OH | OH | $CH_2$ | H | H | H | 1 or 2 |
| CH2OH | H | $CH_2$ | CH2OH | H | H | 1 |
| H | OH | $CH_2$ | H | H | H | 1 or 2 |
| H | OH | CH—OH | H | H | H | 1 or 2 |
| H | NH2 | $CH_2$ | H | H | H | 1 or 2 |
| H | NHMe | $CH_2$ | H | H | H | 1 or 2 |
| H | NMe2 | $CH_2$ | H | H | H | 1 or 2 |
| H | OH | CH—$NH_2$ | H | H | H | 1 or 2 |
| H | OH | CH—NHMe | H | H | H | 1 or 2 |
| H | OH | CH—NH—$CH_2$—CH—OH | H | H | H | 1 or 2 |
| H | H | NH | H | H | H | 1 or 2 |
| H | H | NMe | H | H | H | 1 or 2 |
| H | H | N—$CH_2$—$CH_2$—OH | H | H | H | 1 or 2. |

6. The composition according to claim 5, wherein $R_0$, R1, $Z_4$, R3, R4, and R5 are chosen from the following combinations:

| $R_0$ | $R_1$ | $Z_4$ | $R_3$ | $R_4$ | $R_5$ |
|---|---|---|---|---|---|
| H | H | $CH_2$ | H | H | H |
| COOH | H | $CH_2$ | H | H | H |
| COOH | OH | $CH_2$ | H | H | H |
| CONMe2 | H | $CH_2$ | H | H | H |
| CH2OH | H | $CH_2$ | H | H | H |
| CH2OH | OH | $CH_2$ | H | H | H |
| H | OH | $CH_2$ | H | H | H |
| H | NH2 | $CH_2$ | H | H | H |
| H | H | NH | H | H | H |
| H | H | NMe | H | H | H. |

7. The composition according to claim 1, wherein R6, R7, R8 and R9, which may be identical or different, are chosen from hydrogen atoms, methyl radicals, ethyl radicals, isopropyl radicals, methoxymethyl radicals, hydroxymethyl radicals, 1-carboxymethyl radicals, 1-aminomethyl radicals, 1-aminoethyl radicals, 2-carboxyethyl radicals, 2-hydroxyethyl radicals, 3-hydroxypropyl radicals, 1,2-dihydroxyethyl radicals, 1-hydroxy-2-aminoethyl radicals, 2-hydroxy-1-aminoethyl radicals, methoxy radicals, ethoxy radicals, 3-hydroxyethyloxy radicals and 3-aminoethyloxy radicals.

8. The composition according to claim 7, wherein R6, R7, R8 and R9, which may be identical or different, are chosen from hydrogen atoms, methyl radicals, hydroxymethyl radicals, 2-hydroxyethyl radicals 1,2-dihydroxyethyl radicals, methoxy radicals, 2-hydroxyethoxy radicals.

9. The composition according to claim 8, wherein R6, R7, R8 and R9, which may be identical or different, are chosen from hydrogen atoms, methyl radicals, and methoxy radicals.

10. The composition according to claim 1, wherein R12 and R13, which may be identical or different, are chosen from $C_1$–$C_4$ alkyl radicals, wherein said $C_1$–$C_4$ alkyl radicals are optionally substituted with at least one radical chosen from hydroxyl radicals, $C_1$–$C_2$ alkoxy radicals, amino radicals, $C_1$–$C_2$ (di)alkylamino radicals, carboxyl radicals, and sulfonic radicals.

11. The composition according to claim 10, wherein R12 and R13, which may be identical or different, are chosen from methyl radicals, ethyl radicals, 2-hydroxyethyl radicals, 1-carboxymethyl radicals, 2-carboxyethyl radicals, and 2-sulfonylethyl radicals.

12. The composition according to claim 1, wherein R10 and R11, which may be identical or different, are chosen from hydrogen atoms and $C_1$–$C_4$ alkyl radicals, wherein said $C_1$–$C_4$ alkyl radicals are optionally substituted with at least one radical chosen from hydroxyl radicals, amino radicals, $C_1$–$C_2$ (di)alkylamino radicals, and carboxyl radicals.

13. The composition according to claim 12, wherein R10 and R11, which may be identical or different, are chosen from hydrogen atoms, methyl radicals, ethyl radicals, 2-hydroxyethyl radicals, carboxyl radicals, 1-carboxymethyl radicals, 2-carboxyethyl radicals, and 2-sulfonylethyl radicals.

14. The composition according to claim 1, wherein $Z_1$ is chosen from —NR12 radicals, wherein R12 is defined as in claim 1.

15. The composition according to claim 1, wherein $Z_2$ is chosen from CR11 radicals, wherein R11 is defined as in claim 1.

16. The composition according to claim 1, wherein $Z_4$ is chosen from $NR_2$ and $CR_2R_2'$ groups.

17. The composition according to claim 1, further comprising at least one oxidation base.

18. The composition according to claim 17, wherein said at least one oxidation base is chosen from para-phenylenediamines, bisphenylalkylenediamines, para-aminophenols, ortho-aminophenols, heterocyclic bases, and the acid addition salts thereof.

19. The composition according to claim 17, wherein said at least one oxidation base is present in the composition in an amount ranging from about 0.001% to about 10% by weight, relative to the total weight of the composition.

20. The composition according to claim 19, wherein said at least one oxidation base is present in said composition in an amount ranging from about 0.005% to about 6% by weight, relative to the total weight of the composition.

21. The composition according to claim 1, further comprising at least one coupler.

22. The composition according to claim 21, wherein the at least one coupler is chosen from meta-phenylenediamines, meta-aminophenols, meta-diphenols, naphthalene couplers, heterocyclic couplers and the acid addition salts thereof.

23. The composition according to claim 1, further comprising at least one oxidizing agent.

24. The composition according to claim 23, wherein said at least one oxidizing agent is hydrogen peroxide.

25. A process for the oxidation dyeing of keratinous fibers, comprising applying to said keratinous fibers at least one dyeing composition comprising at least one cationic azo dye of formula (I):

wherein:

$W_1$ is chosen from 5-membered cationic aromatic heterocycles of formula (II):

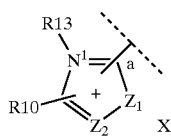

$W_2$ is chosen from divalent carbonaceous aromatic groups and pyridine groups chosen from groups of formulae (III) and (IV):

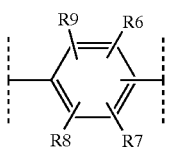

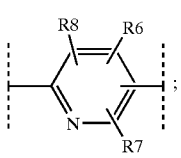

$W_3$ is chosen from 7-membered or 8-membered heterocycles of formula (V):

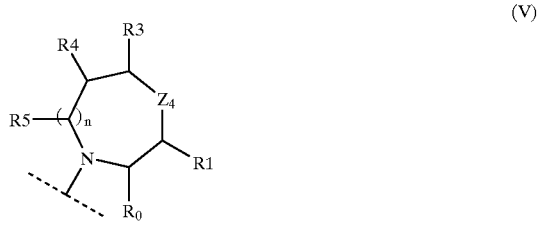

wherein:

$Z_1$ is chosen from oxygen and sulfur atoms, and NR12 radicals;

$Z_2$ is chosen from a nitrogen atom and CR11 radicals;

R12 and R13, which may be identical or different, are chosen from $C_1$–$C_8$ alkyl radicals optionally substituted with at least one radical chosen from hydroxyl radicals, $C_1$–$C_2$ alkoxy radicals, $C_2$–$C_4$ (poly)hydroxyalkoxy radicals, amino radicals, $C_1$–$C_2$ (di)alkylamino radicals, carboxyl radicals, and sulfonic radicals; and optionally substituted phenyl radicals;

R10 and R11, which may be identical or different, are chosen from hydrogen atoms, optionally substituted phenyl radicals, carboxyl radicals, sulfonylamino radicals, and $C_1$–$C_4$ alkyl radicals optionally substituted with at least one radical chosen from hydroxyl radicals, $C_1$–$C_2$ alkoxy radicals, $C_2$–$C_4$ (poly)hydroxyalkoxy radicals, amino radicals, $C_1$–$C_2$ (di)alkylamino radicals, carboxyl radicals, and sulfonic radicals;

R6, R7, R8 and R9, which may be identical or different, are chosen from hydrogen atoms; chlorine atoms; bromine atoms; linear and branched $C_1$–$C_6$ hydrocarbonaceous chains, wherein each of said $C_1$–$C_6$ hydrocarbonaceous chains can form at least one saturated or unsaturated 3- to 6-membered carbonaceous ring, wherein at least one carbon atom of each of said $C_1$–$C_6$ hydrocarbonaceous chains is optionally replaced by an entity chosen from an oxygen atom, a nitrogen atom, a sulfur atom, and $SO_2$ groups and further wherein at least one carbon atom of each of said $C_1$–$C_6$ hydrocarbonaceous chains can be optionally substituted by at least one halogen atom, provided that R6, R7, R8, and R9, which may be identical or different, are not chosen from peroxide bonds, diazo radicals, and nitroso radicals;

n is an integer chosen from 1 and 2;

$Z_4$ is chosen from an oxygen atom, a sulfur atom, $NR_2$ radicals, and $CR_2R_2'$ radicals;

$R_0$, R1, $R_2$, $R_2'$, R3, R4 and R5, which may be identical or different, are chosen from hydrogen atoms; alkyl radicals; alkoxy radicals; hydroxyl radicals; amino radicals; acetoxy radicals; $NR_{14}R_{15}$ groups wherein $R_{14}$ and $R_{15}$, which may be identical or different, are chosen from hydrogen atoms and $C_1$–$C_4$ alkyl radicals substituted with at least one radical chosen from halogen atoms, hydroxyl radicals, $C_1$–$C_2$ alkoxy radicals, amino radicals, and $C_1$–$C_2$ amino(di)alkyl radicals; sulfonylamino radicals; carboxyl radicals; carboxamido radicals; amido radicals; monoalkylamido radicals; dialkylamido radicals; halogen radicals; and $C_1$–$C_6$ alkyl radicals substituted with at least one radical chosen from hydroxyl radicals, $C_1$–$C_2$ alkoxy radicals, $C_2$–$C_4$ (poly)hydroxyalkoxy radicals, amino radicals and $C_1$–$C_2$ (di)alkylamino radicals; and X is chosen from organic anions and inorganic anions.

26. The process according to claim 25, wherein said keratinous fibers are human keratinous fibers.

27. The process according to claim 26, wherein said human keratinous fibers are hair.

28. The process according to claim 25, wherein the at least one dyeing composition comprises at least one oxidizing agent.

29. The process according to claim 28, wherein the at least one oxidizing agent is mixed with the at least one dyeing composition at the time of use.

30. The process according to claim 28, wherein said at least one oxidizing agent is applied to the keratinous fibers in the form of an oxidizing composition simultaneously with or sequentially to the application of said at least one dyeing composition.

31. A process for the oxidation dyeing of keratinous fibers comprising applying to said keratinous fibers, in the presence of at least one oxidizing agent, at least one dyeing composition comprising at least one oxidation base and optionally at least one coupler, and further comprising at least one cationic azo dye of formula (I):

wherein:

$W_1$ is chosen from 5-membered cationic aromatic heterocycles of formula (II):

$W_2$ is chosen from divalent carbonaceous aromatic groups and pyridine groups chosen from groups of formulae (III) and (IV):

$W_3$ is chosen from 7-membered or 8-membered heterocycles of formula (V):

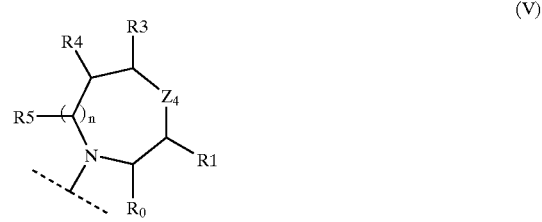

wherein:

$Z_1$ is chosen from oxygen and sulfur atoms, and NR12 radicals;

$Z_2$ is chosen from a nitrogen atom and CR11 radicals;

R12 and R13, which may be identical or different, are chosen from $C_1$–$C_8$ alkyl radicals optionally substituted with at least one radical chosen from hydroxyl radicals, $C_1$–$C_2$ alkoxy radicals, $C_2$–$C_4$ (poly)hydroxyalkoxy radicals, amino radicals, $C_1$–$C_2$ (di)alkylamino radicals, carboxyl radicals, and sulfonic radicals; and optionally substituted phenyl radicals;

R10 and R11, which may be identical or different, are chosen from hydrogen atoms, optionally substituted phenyl radicals, carboxyl radicals, sulfonylamino radicals, and $C_1$–$C_4$ alkyl radicals optionally substituted with at least one radical chosen from hydroxyl radicals, $C_1$–$C_2$ alkoxy radicals, $C_2$–$C_4$ (poly)hydroxyalkoxy radicals, amino radicals, $C_1$–$C_2$ (di)alkylamino radicals, carboxyl radicals, and sulfonic radicals;

R6, R7, R8 and R9, which may be identical or different, are chosen from hydrogen atoms; chlorine atoms; bromine atoms; linear and branched $C_1$–$C_6$ hydrocarbonaceous chains, wherein each of said $C_1$–$C_6$ hydrocarbonaceous chains can form at least one saturated or unsaturated, 3- to 6-membered carbonaceous ring, wherein at least one carbon atom of each of said $C_1$–$C_6$ hydrocarbonaceous chains is optionally replaced by an entity chosen from an oxygen atom, a nitrogen atom, a sulfur atom, and an $SO_2$ radical, and further wherein at least one carbon atom of each of said $C_1$–$C_6$ hydrocarbonaceous chains can be optionally substituted by at least one halogen atom, provided that R6, R7, R8, and R9, which may be identical or different, are not chosen from peroxide bonds, diazo radicals, and nitroso radicals;

n is an integer chosen from 1 and 2;

$Z_4$ is chosen from an oxygen atom, a sulfur atom, $NR_2$ radicals, and $CR_2R_2'$ radicals;

$R_0$, R1, $R_2$, $R_2'$, R3, R4 and R5, which may be identical or different, are chosen from hydrogen atoms; alkyl radicals; alkoxy radicals; hydroxyl radicals; amino radicals; acetoxy radicals; $NR_{14}R_{15}$ groups wherein $R_{14}$ and $R_{15}$, which may be identical or different, are chosen from hydrogen atoms and $C_1$–$C_4$ alkyl radicals substituted with at least one radical chosen from halogen atoms, hydroxyl radicals, $C_1$–$C_2$ alkoxy radicals, amino radicals, and $C_1$–$C_2$ amino(di)alkyl radicals; sulfonylamino radicals; carboxyl radicals; carboxamido radicals; amido radicals; monoalkylamido radicals; dialkylamido radicals; halogen radicals; and $C_1$–$C_6$ alkyl radicals substituted with at least one radical chosen from hydroxyl radicals, $C_1$–$C_2$ alkoxy radicals, $C_2$–$C_4$ (poly)hydroxyalkoxy radicals, amino radicals and $C_1$–$C_2$ (di)alkylamino radicals; and X is chosen from organic anions and inorganic anions.

32. The process according to claim 31, wherein said keratinous fibers are human keratinous fibers.

33. The process according to claim 32, wherein said human keratinous fibers are hair.

34. The process according to claim 31 wherein, at the time of use, said at least one oxidizing agent is mixed with said at least one dyeing composition.

35. The process according to claim 31, wherein said at least one oxidizing agent is applied to said keratinous fibers in the form of an oxidizing composition simultaneously with or sequentially to the application of said at least one dyeing composition.

36. A multi-compartment dyeing device comprising at least one compartment comprising at least one dyeing composition for keratinous fibers and at least one compartment comprising at least one oxidizing composition, wherein said dyeing composition comprises at least one cationic azo dye of formula (I):

wherein:

$W_1$ is chosen from 5-membered cationic aromatic heterocycles of formula (II):

$W_2$ is chosen from divalent carbonaceous aromatic groups and pyridine groups chosen from groups of formulae (III) and (IV):

$W_3$ is chosen from 7-membered or 8-membered heterocycles of formula (V):

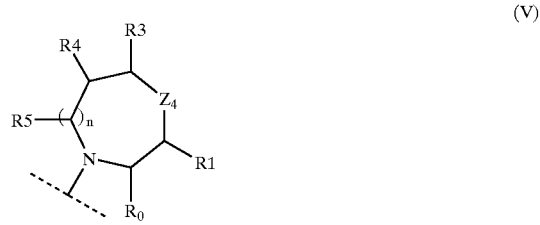

wherein:

$Z_1$ is chosen from oxygen and sulfur atoms, and NR12 radicals;

$Z_2$ is chosen from a nitrogen atom and CR11 radicals;

R12 and R13, which may be identical or different, are chosen from $C_1$–$C_8$ alkyl radicals optionally substituted with at least one radical chosen from hydroxyl radicals, $C_1$–$C_2$ alkoxy radicals, $C_2$–$C_4$ (poly) hydroxyalkoxy radicals, amino radicals, $C_1$–$C_2$ (di) alkylamino radicals, carboxyl radicals, and sulfonic radicals; and optionally substituted phenyl radicals;

R10 and R11, which may be identical or different, are chosen from hydrogen atoms, optionally substituted phenyl radicals, carboxyl radicals, sulfonylamino radicals, and $C_1$–$C_4$ alkyl radicals that are optionally substituted with at least one radical chosen from hydroxyl radicals, $C_1$–$C_2$ alkoxy radicals, $C_2$–$C_4$ (poly) hydroxyalkoxy radicals, amino radicals, $C_1$–$C_2$ (di) alkylamino radicals, carboxyl radicals, and sulfonic radicals;

R6, R7, R8 and R9, which may be identical or different, are chosen from hydrogen atoms; chlorine atoms; bromine atoms; linear and branched $C_1$–$C_6$ hydrocarbonaceous chains, wherein each of said $C_1$–$C_6$ hydrocarbonaceous chains can form at least one saturated or unsaturated, 3- to 6-membered carbonaceous ring, wherein at least one carbon atom of each of said $C_1$–$C_6$ hydrocarbonaceous chains is optionally replaced by an entity chosen from an oxygen atom, a nitrogen atom, a sulfur atom, and an $SO_2$ radical and further wherein at least one carbon atom of each of said $C_1$–$C_6$ hydrocarbonaceous chains can be optionally substituted by at least one halogen atom, provided that R6, R7, R8, and R9, which may be identical or different, are not chosen from peroxide bonds, diazo radicals, and nitroso radicals;

n is an integer chosen from 1 and 2;

$Z_4$ is chosen from an oxygen atom, a sulfur atom, $NR_2$ radicals, and $CR_2R_2'$ radicals;

$R_0$, R1, $R_2$, $R_2'$, R3, R4 and R5, which may be identical or different, are chosen from hydrogen atoms; alkyl radicals; alkoxy radicals; hydroxyl radicals; amino radicals; acetoxy radicals; $NR_{14}R_{15}$ groups wherein $R_{14}$ and $R_{15}$, which may be identical or different, are chosen from hydrogen atoms and $C_1$–$C_4$ alkyl radicals substituted with at least one radical chosen from halogen atoms, hydroxyl radicals, $C_1$–$C_2$ alkoxy radicals, amino radicals, and $C_1$–$C_2$ amino(di)alkyl radicals; sulfonylamino radicals; carboxyl radicals; carboxamido radicals; amido radicals; monoalkylamido radicals; dialkylamido radicals; halogen radicals; and $C_1$–$C_6$ alkyl radicals substituted with at least one radical chosen from hydroxyl radicals, $C_1$–$C_2$ alkoxy radicals, $C_2$–$C_4$ (poly)hydroxyalkoxy radicals, amino radicals and $C_1$–$C_2$ (di)alkylamino radicals; and X is chosen from organic anions and inorganic anions.

37. A cationic azo compound chosen from compounds of formula (I):

wherein:

W$_1$ is chosen from 5-membered cationic aromatic heterocycles of formula (II):

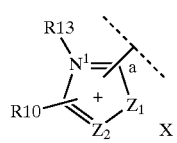

W$_2$ is chosen from divalent carbonaceous aromatic groups and pyridine groups chosen from groups of formulae (III) and (IV):

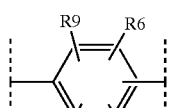

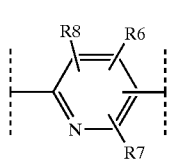

W$_3$ is chosen from 7-membered or 8-membered heterocycles of formula (V):

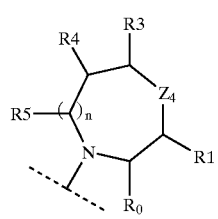

wherein:

Z$_1$ is chosen from oxygen and sulfur atoms, and NR12 radicals;

Z$_2$ is chosen from a nitrogen atom and CR11 radicals;

R12 and R13, which may be identical or different, are chosen from $C_1$–$C_8$ alkyl radicals optionally substituted with at least one radical chosen from hydroxyl radicals, $C_1$–$C_2$ alkoxy radicals, $C_2$–$C_4$ (poly) hydroxyalkoxy radicals, amino radicals, $C_1$–$C_2$ (di) alkylamino radicals, carboxyl radicals, and sulfonic radicals; and optionally substituted phenyl radicals;

R10 and R11, which may be identical or different, are chosen from hydrogen atoms, optionally substituted phenyl radicals, carboxyl radicals, sulfonylamino radicals, and $C_1$–$C_4$ alkyl radicals optionally substituted with at least one radical chosen from hydroxyl radicals, $C_1$–$C_2$ alkoxy radicals, $C_2$–$C_4$ (poly) hydroxyalkoxy radicals, amino radicals, $C_1$–$C_2$ (di) alkylamino radicals, carboxyl radicals, and sulfonic radicals;

R6, R7, R8 and R9, which may be identical or different, are chosen from hydrogen atoms; chlorine atoms; bromine atoms; linear and branched $C_1$–$C_6$ hydrocarbonaceous chains, wherein each of said $C_1$–$C_6$ hydrocarbonaceous chains can form at least one saturated or unsaturated, 3- to 6-membered carbonaceous ring, wherein at least one carbon atom of each of said $C_1$–$C_6$ hydrocarbonaceous chains is optionally replaced by an entity chosen from an oxygen atom, a nitrogen atom, a sulfur atom, and an SO$_2$ radical and further wherein at least one carbon atom of each of said $C_1$–$C_6$ hydrocarbonaceous chains can be optionally substituted by at least one halogen atom, provided that R6, R7, R8, and R9, which may be identical or different, are not chosen from peroxide bonds, diazo radicals, and nitroso radicals;

n is an integer chosen from 1 and 2;

Z$_4$ is chosen from an oxygen atom, a sulfur atom, NR$_2$ radicals, and CR$_2$R$_2$' radicals;

R$_0$, R1, R$_2$, R$_2$', R3, R4 and R5, which may be identical or different, are chosen from hydrogen atoms; alkyl radicals; alkoxy radicals; hydroxyl radicals; amino radicals; acetoxy radicals; NR$_{14}$R$_{15}$ groups wherein R$_{14}$ and R$_{15}$, which may be identical or different, are chosen from hydrogen atoms and $C_1$–$C_4$ alkyl radicals substituted with at least one radical chosen from halogen atoms, hydroxyl radicals, $C_1$–$C_2$ alkoxy radicals, amino radicals, and $C_1$–$C_2$ amino(di)alkyl radicals; sulfonylamino radicals; carboxyl radicals; carboxamido radicals; amido radicals; monoalkylamido radicals; dialkylamido radicals; halogen radicals; and $C_1$–$C_6$ alkyl radicals substituted with at least one radical chosen from hydroxyl radicals, $C_1$–$C_2$ alkoxy radicals, $C_2$–$C_4$ (poly)hydroxyalkoxy radicals, amino radicals and $C_1$–$C_2$ (di)alkylamino radicals; and X is chosen from organic anions and inorganic anions.

* * * * *

UNITED STATES PATENT AND TRADEMARK OFFICE
CERTIFICATE OF CORRECTION

PATENT NO. : 6,881,230 B2 Page 1 of 1
DATED : April 19, 2005
INVENTOR(S) : Laurent Vidal It is certified that error appears in the above-identified patent and that said Letters Patent is hereby corrected as shown below:

Column 13,
Lines 38 and 39, "CONH2" should read -- $CONH_2$ --.
Lines 40, 41 and 65, "CONMe2" should read -- $CONMe_2$ --.
Lines 42, 43, 44 and 66, "CH2OH" should read -- $CH_2OH$ --.
Line 46, NH2" should read -- $NH_2$ --.
Line 48, "NMe2" should read -- $NMe_2$ --.

Column 14,
Line 5, "CONMe2" should read -- $CONMe_2$ --.
Line 7 (all occurrences), "CH2OH" should read -- $CH_2OH$ --.
Line 7, "NH2" should read -- $NH_2$ --.

Signed and Sealed this

Sixteenth Day of August, 2005

JON W. DUDAS
*Director of the United States Patent and Trademark Office*